United States Patent [19]
Anderson et al.

[11] Patent Number: 5,851,237
[45] Date of Patent: Dec. 22, 1998

[54] OXIDATIVE HAIR DYE COMPOSITIONS AND METHODS CONTAINING 1—(4-AMINOPHENYL) PYRROLIDINES

[76] Inventors: James S. Anderson, 1 Summit La., Bethel, Conn. 06801; Michael Y. M. Wong, 226 Adams Rd., Easton, Conn. 06612

[21] Appl. No.: 892,339

[22] Filed: Jul. 14, 1997

[51] Int. Cl.$^6$ ....................................................... A61K 7/13
[52] U.S. Cl. ........................... 8/409; 8/408; 8/410; 8/411; 8/412; 8/423; 8/574
[58] Field of Search ................................ 8/406, 408, 409, 8/410, 411, 412, 416, 423, 574; 548/577, 579

[56] References Cited

U.S. PATENT DOCUMENTS 4,131,468  12/1978  Rennison et al. ....................... 430/160
5,278,034  1/1994  Ohki et al. ............................... 430/440

*Primary Examiner*—Paul Lieberman
*Assistant Examiner*—Caroline D. Liott
*Attorney, Agent, or Firm*—Morton S. Simon

[57] ABSTRACT

The invention provides compositions and methods for the oxidative coloring of human hair. The compositions of the invention contain as a primary dye intermediate a 1-(4-aminophenyl) pyrrolidine, or a cosmetically acceptable salt thereof. The compositions may also contain at least one other primary intermediate and conventional coupling compounds, in addition to an oxidizing agent and other components typically used in oxidative hair dye preparations. Preferred dye intermediates in the compositions of the invention include 1-(4-aminophenyl) pyrrolidine and 1-(4-amino-3-methylphenyl) pyrrolidine, or cosmetically acceptable salts thereof, which produce intense neutral colors when used in admixture with a suitable coupling agents, such as 3-aminophenol, in conventional hair dye base formulations.

30 Claims, No Drawings

OXIDATIVE HAIR DYE COMPOSITIONS AND METHODS CONTAINING 1—(4-AMINOPHENYL) PYRROLIDINES

FIELD OF THE INVENTION

The invention relates generally to methods and compositions for preparing stable oxidative hair dyes that result in long-lasting and true color and do not adversely affect the texture and condition of the hair after application. The present invention more particularly relates to oxidative hair dye compositions and methods comprising 1-(4-aminophenyl) pyrrolidines, as primary intermediates, in addition to other conventionally-used additives and components.

BACKGROUND OF THE INVENTION

Oxidative hair dye colorants are essential elements in hair dyeing preparations for the permanent dyeing of human hair. The hair dyeing process is achieved, in general, by the reaction of certain developing compounds with certain coupling compounds in the presence of a suitable oxidizing agent or compound, such as hydrogen peroxide.

When oxidation dyes, such as those comprising primary intermediates, and couplers are used in the dyeing of human hair, the procedure may involve the use of a two part system. In general, one part can be a lotion formulation which contains a variety of ingredients, including oxidation dye precursors (i.e., primary intermediates and coupling agents). The other part is a developer formulation containing a suitable oxidizing agent, e.g., hydrogen peroxide. Immediately prior to application to the hair, the two parts are mixed to form a thickened liquid solution, for example, a lotion or a gel. As a consequence of the oxidizing properties of the oxidizing agent, some of the natural melanin pigment of the hair may be bleached. The precursors in the thickened solution (e.g., lotion or gel) penetrate into the hair and are oxidized to produce the desired color. Such systems generally contain a proportion of organic solvents and surfactants and contain relatively high levels of dye precursors to produce the desired color.

In order for procedures using permanent oxidative dyes to work properly, a number of parameters and conditions are important to consider in the use of these dyes in admixture with couplers in hair color preparations for human hair. Among these are the final color and color intensity that are produced after application to the subject's hair; the wash fastness and the light fastness of the resulting dye; the resistance of the dye to perspiration; the type of hair being dyed, e.g., virgin hair or waved hair; the resistance of the dye to various hair treatments, such as permanent wave, straightening, shampooing, conditioning and rubbing. In addition, the dye must have virtually no allergenicity or dermal or systemic toxicity.

1,4-benzenediamine (i.e., para-phenylenediamine or PPD) is a primary intermediate widely used in oxidative hair dye compositions. When coupled with a conventional coupling agent, such as 3-aminophenol, it forms a unique color which is very intense in depth, yet neutral in shade. However, PPD is known to be both an allergen and a sensitizer. Therefore, needed in the art are primary intermediates that are capable of forming the unique color and shade performance of PPD, but which are more toxicologically benign. Such new primary intermediates can be used to replace PPD or used in conjunction with PPD, in whole or in part.

Until the present invention, no primary dye intermediate has been found as a dye component, which generates a quality of color that is comparable or equivalent to that produced by PPD when used with coupling substances as color modifiers. In addition, no primary dye intermediate, as a supplement or replacement for PPD, has to date been found which satisfies the above-listed requirements for oxidative colorants used in the dyeing of human hair.

U.S. Pat. No. 4,840,639 to H. Husemeyer et al. discloses hydroxyalkyl-substituted PPDs, namely, the 1-hydroxyalkyl-2,5-diaminobenzenes, such as 2-(2-hydroxyethyl) PPD, as a developing agent in oxidative hair dyes. GB 1,025,916 to L'Oreal discloses compounds such as 1-(4-aminophenyl) piperidine or 4-(4-aminophenyl) morpholine, and couplers, in hair dye compositions and methods.

The electrochemical, photographic, allergenic and coupling properties of 1-(4-aminophenyl) pyrrolidine is disclosed by R. L. Bent et al., *J. Am. Chem. Soc.*, 73:3100–3125, 1951 (Kodak Research Labs), in a long list of p-amino-N-allylaniline compounds used in color photographic processes (Table I of Bent et al.). The report of Bent et al. is strictly germane to the photographic arts and does not teach or contemplate the use of primary dye intermediates in the oxidative coloring of hair. Similarly, L. K. J. Tong et al., *J. Am. Chem. Soc.*, 82:1988–1996, 1959 (Kodak Research Labs), report the deamination of oxidized derivatives of p-phenylenediamines (Table I of Tong et al.). The studies of Tong et al. were carried out, in an unrelated field of art, in an effort to understand the mechanism of dye formation in connection with photographic image production.

The compounds of the present invention, which are of the class of 1-(4-aminophenyl) pyrrolidines, or cosmetically acceptable salts thereof, are clearly distinct from photographic and hair dyeing compounds disclosed in the prior art and offer newly-discovered and advantageous hair coloring properties.

SUMMARY OF THE INVENTION

It is an object of the invention to provide oxidative hair dye compositions and methods comprising compounds of the class of 1-(4-aminophenyl) pyrrolidines, or cosmetically acceptable salts thereof, as primary intermediates in compositions comprising such primary dye intermediates as well as coupling agents, oxidizing agents and other adjuvant substances. In accordance with a particular aspect of the invention 1-(4-aminophenyl) pyrrolidine is preferred.

It is yet another object of the invention to provide compositions and methods for the oxidative coloration of hair comprising one or more novel primary dye intermediate compounds of the 1-(4-aminophenyl) pyrrolidine class of compounds, this class being toxicologically benign to the user.

It is a further object of the invention to provide 1-(4-aminophenyl) pyrrolidine compounds that serve as effective and high-performance primary intermediates in oxidative hair dyes. The 1-(4-aminophenyl) pyrrolidine compounds of the invention are capable of replacing, in whole or in part, paraphenylenediamine (PPD), a known allergen and a sensitizer, employed with couplers as color modifiers in such hair dye formulations.

Yet another object of the invention is to provide a newly-discovered primary dye intermediate, 1-(4-amino-3-methylphenyl) pyrrolidine, or a cosmetically acceptable salt thereof, which provides intense color when used in oxidative hair dye compositions in combination with coupling agents, oxidizing agents and other hair dye additives and/or adjuvants conventionally used in hair dye formulations for the dyeing of hair.

Further objects and advantages afforded by the invention will be apparent from the detailed description hereinbelow.

DETAILED DESCRIPTION OF THE INVENTION

The present invention provides novel compounds which are primary intermediates for use in oxidative hair dye compositions. The compositions of the present invention include, as primary dye intermediates, one or more components from the chemical class of substituted or unsubstituted 1-(4-aminophenyl) pyrrolidine compounds, and derivatives and cosmetically acceptable salts thereof. Nonlimiting examples of derivatives and salts of the 1-(4-aminophenyl) pyrrolidine compounds include sulfates, hydrochlorides, phosphates and the like, with sulfates being preferred. The 1-(4-aminophenyl) pyrrolidine compounds of the present invention are generally represented by the following chemical formula I:

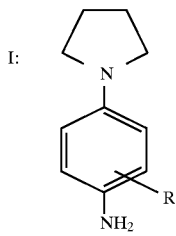

wherein R is a hydrogen (H) atom; $C_1$–$C_6$ alkyl, preferably $C_1$–$C_4$ alkyl more preferably $C_1$–$C_2$ alkyl; or $C_1$–$C_4$ mono- or polyhydroxyalkyl preferably $C_1$–$C_3$ monohydroxyalkyl. Preferred are unsubstituted 1-(4-aminophenyl) pyrrolidine (e.g., formula I, wherein R is hydrogen), as well as substituted 1-(4-aminophenyl) pyrrolidines, (e.g., formula I, wherein R is methyl or ethyl).

In accordance with the present invention, substituted 1-(4-aminophenyl) pyrrolidines useful as primary dye intermediates in the hair coloring compositions of the invention include 1-(4-amino-2-methylphenyl) pyrrolidine and 1-(4-amino-3-methylphenyl) pyrrolidine or cosmetically acceptable salts thereof, for example, 1-(4-amino-2-methylphenyl) pyrrolidine sulfate and 1-(4-amino-3-methylphenyl) pyrrolidine sulfate, respectively. 1-(4-amino-2-methylphenyl) pyrrolidine and 1-(4-amino-3-methylphenyl) pyrrolidine have the structures depicted below as formulae II and III, respectively:

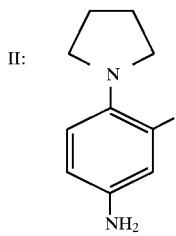

-continued

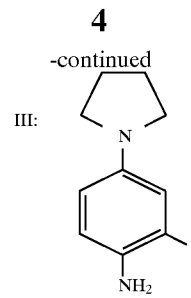

Although compounds II and III are 1-(4-aminophenyl) pyrrolidines substituted with a methyl group, it was discovered that the placement of a methyl group at the 3 position of the phenyl ring resulted in a unique primary intermediate which afforded a deeper and richer shade of color to dyed hair and surprisingly exceeded the quite acceptable and useful coloring performance of the 4-aminophenyl pyrrolidine compound substituted with a methyl group at position 2 of the phenyl ring. Accordingly, both the substituted and unsubstituted 4-aminophenyl pyrrolidine compounds proved to be effective as primary dye intermediates with other hair dye components in oxidative hair dye compositions of the present invention.

A preferred unsubstituted 4-aminophenyl pyrrolidine compound of the present invention is 1-(4-aminophenyl) pyrrolidine, which is represented by the following formula IV:

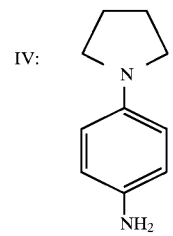

The compositions of the present invention contain as a primary dye intermediate one or more substituted or unsubstituted 1-(4-aminophenyl) pyrrolidine compounds, or a cosmetically acceptable salt thereof, which may be present in admixture with one or more other dye component(s), for example, a primary dye intermediate, e.g., PPD, or conventional coupling component(s), in addition to other hair dye component ingredients, additives, or adjuvants typically used in oxidative hair dye formulations as described herein. The 1-(4-aminophenyl) pyrrolidines, alone or in combination with one or more other dye intermediates and coupling agents produce novel dyestuffs which provide intense coloration to hair. The 1-(4-aminophenyl) pyrrolidine compounds of the present invention achieve a deep coloration to hair and impart unique properties to dye substances used for oxidative hair coloring.

It will be appreciated by those having skill in the art that the compositions and methods of the present invention are appropriate for the dyeing of keratinous fibers, including the hair fibers of animals and humans, with particular application to the oxidative coloring of human hair.

In accordance with the present invention, members of the class of 1-(4-aminophenyl) pyrrolidine primary dye intermediate compounds have been discovered to be similar in coloring capacity to the conventionally-used primary intermediate PPD, i.e., to exhibit the same color and intensity when used in an oxidative hair dye product with a coupling compound as color modifier in hair dye formulations (Table 4).

The 1-(4-aminophenyl) pyrrolidines of the present invention and their cosmetically acceptable derivatives or salts afford particularly significant advantages as primary intermediates in dye compositions. These compounds can be used as substitutes for PPD and to replace PPD, in whole or in part, in dye compositions. For example, the compositions of the present invention formulated to contain 1-(4-aminophenyl) pyrrolidine, or a cosmetically acceptable derivative or salt thereof, for the oxidative dyeing of hair, afford outstanding effectiveness as colorants, with fewer adverse side effects than like compositions containing PPD. In addition, the present compositions satisfy the dermatological and toxicological requirements that should optimally be met by oxidative coloring substances, particularly for the coloring of human hair.

As described above, in addition to at least one of the novel component dye molecules encompassed by the present invention, the hair dyeing compositions described herein may also contain at least one other known and usual dye ingredient (i.e., used as primary dye intermediates and/or couplers), as well as conventional direct-acting colorants and dyes in admixture, should these substances be necessary or desired for the development and production of certain color nuances and tints.

Illustrative component dye ingredients that are conventionally admixed and employed as constituents of customary hair dye formulations and that can be considered suitable for use in the compositions of the present invention are set forth hereinbelow. As but one particular example, p-phenylenediamine, used in oxidative hair coloring formulations, may conveniently be used in admixture with the novel primary intermediate 1-(4-aminophenyl) pyrrolidine compounds in the compositions of the present invention.

Included among the suitable dye components that may be considered for use as primary intermediates and/or couplers in the dye compositions of the present invention are the following: p-phenylenediamine derivatives such as: p-toluenediamine; p-phenylenediamine; 2-chloro-p-phenylenediamine; N-phenyl-p-phenylenediamine; N-2-methoxyethyl-p-phenylenediamine; N,N-bis-hydroxyethyl-p-phenylenediamine; 2-hydroxymethyl-p-phenylenediamine; 2-hydroxyethyl-p-phenylenediamine; 4,4'-diaminodiphenylamine; 2,6-dimethyl-p-phenylenediamine; 2-isopropyl-p-phenylenediamine; N-(2-hydroxypropyl)-p-phenylenediamine; 2-propyl-p-phenylenediamine; 1,3-bis-(N-hydroxyethyl)-N-(4-aminophenyl)amino)-2-propanol; and 2-methyl-4-dimethylaminoaniline, or combinations thereof.

Preferred p-phenylenediamine derivatives include: p-toluenediamine; p-phenylenediamine; N-2-methoxyethyl-p-phenylenediamine; N,N-bis-hydroxyethyl-p-phenylenediamine; and 2-hydroxyethyl-p-phenylenediamine.

p-Aminophenol derivatives include: p-aminophenol; p-methylaminophenol; 3-methyl-p-aminophenol; 2-hydroxymethyl-p-aminophenol; 2-methyl-p-aminophenol; 2-(2'-hydroxyethylaminomethyl)-p-aminophenol; 2-methoxymethyl-p-aminophenol; and 5-aminosalicylic acid, or combinations thereof.

Preferred p-aminophenol derivatives include: p-aminophenol; p-methylaminophenol; 3-methyl-p-aminophenol; 2-methyl-p-aminophenol; 2-(2'-hydroxyethylaminomethyl)-p-aminophenol; 2-methoxymethyl-p-aminophenol; and 5-aminosalicylic acid.

Ortho developers include: catechol; pyrogallol; o-aminophenol; 2,4-diaminophenol; 2,4,5-trihydroxytoluene; 1,2,4-trihydroxybenzene; 2-ethylamino-p-cresol; 2,3-dihydroxynaphthalene; 5-methyl-o-aminophenol; 6-methyl-o-aminophenol; and 2-amino-5-acetaminophenol, or combinations thereof.

Preferred ortho developers include: o-aminophenol; 2,4-diaminophenol; 2,4,5-trihydroxytoluene; 1,2,4-trihydroxybenzene; 2-ethylamino-p-cresol; 5-methyl-o-aminophenol; 6-methyl-o-aminophenol; and 2-amino-5-acetaminophenol.

Phenols and resorcinol derivatives include: 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; hydroquinone; 2-methylresorcinol; 1-hydroxy-6-aminonaphthalene-3-sulfonic acid; thymol (2-isopropyl-5-methylphenol); 1,5-dihydroxy-1,2,3,4-tetrahydronaphthalene; 2-chlororesorcinol; 2,3-dihydroxy-1,4-naphthoquinone; and 1-naphthol-4-sulfonic acid, or combinations thereof.

Preferred phenols and resorcinol derivatives include: 2-methyl-1-naphthol; 1-acetoxy-2-methylnaphthalene; 1,7-dihydroxynaphthalene; resorcinol; 4-chlororesorcinol; 1-naphthol; 1,5-dihydroxynaphthalene; 2,7-dihydroxynaphthalene; hydroquinone; 2-methylresorcinol; thymol (2-isopropyl-5-methylphenol); and 2,3-dihydroxy-1,4-naphthoquinone.

m-Phenylenediamines include: m-phenylenediamine; 2-(2,4-diaminophenoxyethanol; N,N-(bis-hydroxyethyl) m-phenylenediamine; 2,6-diaminotoluene; $N^2$-bis-hydroxyethyl-2,4-diaminophenetole; bis-(2,4-diaminophenoxy)-1,3-propane; hydroxyethyl-2,4-diaminobenzene; 2-amino-4-hydroxyethylamino anisole; aminoethyloxy-2,4-diaminobenzene; 2,4-diaminophenoxyacetic acid; 4,6-(bis-hydroxyethyloxy) m-phenylenediamine; 2,4-diamino-5-methylphenetole; 2,4-diamino-5-hydroxyethyloxytoluene; 2,4-dimethoxy-1,3-diaminobenzene; and 2,6-(bis-hydroxyethylamino) toluene, or combinations thereof.

Preferred m-phenylenediamines include: m-phenylenediamine; 2,4-diaminophenoxyethanol; bis-(2,4-diaminophenoxy)-1,3-propane; hydroxyethyl-2,4-diaminobenzene; 2-amino-4-hydroxyethylamino anisole; 4,6-bis-hydroxyethyloxy-m-phenylenediamine; 2,4-diamino-5-methylphenetole; 2,4-diamino-5-hydroxyethyloxytoluene; 2,4-dimethoxy-1,3-diaminobenzene; and 2,6-(bis-hydroxyethylamino) toluene.

m-Aminophenols include: m-aminophenol; 2-hydroxy-4-carbamoylmethylamino toluene; m-carbamoylmethylamino phenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 2-hydroxyethyloxy-5-aminophenol; 2-chloro-5-trifluoroethylaminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol, or combinations thereof.

Preferred m-aminophenols include: m-aminophenol; 6-hydroxybenzomorpholine; 2-hydroxy-4-aminotoluene; 2-hydroxy-4-hydroxyethylaminotoluene; 4,6-dichloro-m-aminophenol; 2-methyl-m-aminophenol; 2-chloro-6-methyl-m-aminophenol; 4-chloro-6-methyl-m-aminophenol; N-cyclopentyl-3-aminophenol; N-hydroxyethyl-4-methoxy-2-methyl-m-aminophenol and 5-amino-4-methoxy-2-methylphenol.

Heterocyclic derivatives include: 2-dimethylamino-5-aminopyridine; 2,4,5,6-tetra-aminopyrimidine; 4,5- diamino-1-methyl-pyrazole; 1-phenyl-3-methyl-5-pyrazolone; 6-methoxy-8-aminoquinoline; 2,6-dihydroxy-4-methylpyridine; 5-hydroxy-1,4-benzodioxane; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 2,6-bis-hydroxyethyloxy-3,5-diaminopyridine; 4-hydroxyindole; 3-amino-5-hydroxy-2,6-dimethoxypyridine; 5,6-dihydroxyindole; 7-hydroxyindole; 5-hydroxyindole; 2-bromo-4,5-methylenedioxyphenol; 6-hydroxyindole; isatin (indole-2,3-dione); 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine, or combinations thereof.

Preferred heterocyclic derivatives include: 4,5-diamino-1-methyl-pyrazole; 2-dimethylamino-5-aminopyridine; 2,4,5,6-tetra-aminopyrimidine; 1-phenyl-3-methyl-5-pyrazolone; 3,4-methylenedioxyphenol; 4-hydroxyethylamino-1,2-methylenedioxybenzene; 2,6-dihydroxy-3,4-dimethylpyridine; 5-chloro-2,3-dihydroxypyridine; 3,5-diamino-2,6-dimethoxypyridine; 2-hydroxyethylamino-6-methoxy-3-aminopyridine; 3,4-methylenedioxyaniline; 4-hydroxyindole; 5,6-dihydroxyindole; 7-hydroxyindole; 5-hydroxyindole; 2-bromo-4,5-methylenedioxyphenol; 6-hydroxyindole; isatin (indole-2,3-dione); 3-amino-2-methylamino-6-methoxypyridine; 2-amino-3-hydroxypyridine; 2,6-diaminopyridine; 5-(3,5-diamino-2-pyridyloxy)-1,3-dihydroxypentane; 3-(3,5-diamino-2-pyridyloxy)-2-hydroxypropanol and 4-hydroxy-2,5,6-triaminopyrimidine.

The additional dye compounds, e.g., couplers, should be present in the hair dyeing compositions of the present invention in an amount of approximately 0.01 to 10%, by weight, preferably approximately 0.1 to 5%, by weight, based on the total weight of the composition. The total quantity of oxidative colorant, comprising dye substance(s) and coupling substance(s) will suitably amount to approximately 0.1 to 10%, by weight, and preferably, approximately 0.5 to 5% by weight, based on the total weight of the composition.

Unless indicated otherwise, as used herein, reagent or component amounts are in % by weight (w/w), based on the total weight of the composition.

In the compositions of the present invention, the coupling component is generally used in approximately equimolar amounts relative to the developing component. However, it will be appreciated that the dye component, in relation to the coupler, may be present either in increased or decreased amounts depending upon the formulation and the desired color, intensity or effect. In general terms, the dye component and the coupling component, or cosmetically acceptable salts thereof, will be present in tinctorially effective amounts for the coloring of a hair fiber.

The hair dye preparations of the present invention may be formulated into cosmetic preparations such as a solution, cream, lotion, gel or emulsion. Also, in accordance with the invention, the compositions may represent a mixture of the coloring components (i.e., dye intermediate and coupling agent) in with other components commonly associated with the formulation of solutions, creams, lotions, gels or emulsions, and the like. For example, components such as wetting agents or emulsifying agents from the categories of anionic or non-ionic surfactants, such as sulfates of fatty alcohols, alkanolamides of fatty alcohols, alkyl sulfonates, alkylbenzene sulfonates, oxyethylated fatty alcohols, oxyethylated nonylphenols; furthermore thickeners such a fatty alcohols, starch, cellulose derivatives, paraffin oil and fatty acids, as well as hair-care substances such as lanolin derivatives, cholesterol and pantothenic acid, may be formulated into the compositions of the invention.

As an example, if formulated as a lotion, the compositions of the invention may contain organic solvents to assist in dissolving the dye precursors. Accordingly, the organic solvent content of the lotion may be from 0% to about 20%, preferably, about 1% to about 15%. Typically useful solvents include alcohols containing up to three carbon atoms such as ethanol and isopropanol, polyhydroxy alcohols such as propylene or hexylene glycol and lower alkyl ethers thereof, such as ethoxy ethers.

In addition, the hair dyeing compositions in accordance with the present invention may optionally contain conventionally-used adjuvants and cosmetic additives, or mixtures thereof, to achieve the final formulations. Examples of such additives include, but are not limited to, anti-oxidants, e.g., ascorbic acid, erythoboric acid, or sodium sulfite, to inhibit premature oxidizing; oxidizing agents; fragrances and/or perfume oils; chelating agents; emulsifiers; coloring agents; thickeners; organic solvents; opacifying agents; dispersing agents; sequestering agents; hair-care substances; humectants; and anti-microbials, and others. The list of optional ingredients is not intended as limiting. Other suitable adjuvants for inclusion in the hair dye compositions of the invention are disclosed, for example, in Zviak, *The Science of Hair Care* (1986) and in Balsam and Sagarin, Cosmetics: *Science and Technology*, Vol. 2, Second Edition, (1972).

More specifically, organic solvents used in the hair dye compositions assist in dissolving the dyes. Typically useful solvents include, but are not limited to, alcohols containing up to three carbon atoms, such as ethanol and isopropanol, as well as polyhydroxy alcohols, such as propylene glycol and hexylene glycol. Lower alkyl ethers, such as ethoxy diglycol may be used.

Thickeners that may be used in the compositions of the present invention include a variety of fatty acid soaps and associative polymeric thickeners. The fatty acid soaps are alkaline metal salts or alkanolamine salts of fatty acids with $C_{10}$–$C_{16}$ alkyl side chains. The preferred fatty acids include oleic acid, myristic acid and lauric acid, which are generally present in the compositions of the invention at about 0.5% to about 20%, preferably about 1% to about 10%. Associative thickeners are polymers that can thicken solutions at low concentrations. Among the associative thickeners that are useful in the compositions of the present invention are acrylates copolymer (sold by Rohm and Haas under the tradename Aculyn-33), ceteareth-20 acrylates/steareth-20 methacrylate copolymer (sold by Rohm and Haas under the Trade Name Aculyn-22), acrylates/steareth-20 itaconate copolymer and acrylates/ceteth-20 itaconate copolymer. Another class of associative thickeners that is useful in the compositions of the present invention include the copolymers of polyurethane and polyethylene glycol or polyether urethanes. One such material is sold by Rohm and Haas under the tradename Aculyn-44. The associative polymeric thickeners are generally present in the compositions of the invention at about 0.1% to about 10%, preferably, about 0.5% to about 5%.

The oxidative coupling, i.e., the development of the dye, to produce the final color product on the hair, can, in principle, be performed with atmospheric oxygen. However, chemical oxidizing agents are suitably and preferably used. Although other oxidizing agents can be employed, hydrogen peroxide is a preferred oxidizing compound for use as a developer with the primary intermediate and coupler dye precursors of the invention. The concentration of hydrogen peroxide in the developer may be from about 1% to about 15%, preferably, from about 3% to about 12%. Other suitable oxidizing agents include, for example, urea peroxide, melamine peroxide, perborates and percarbonates such as sodium perborate or percarbonate. The amounts of such oxidizing agents can be routinely determined by one having skill in the art, without requiring any inventive skill.

The compositions of the invention may include a typical anionic, cationic, nonionic or amphoteric surfactant. The anionic surfactants include the variety of alkyl sulfates, alkylether sulfates, alkyl sulfonates, alkyl sulfosuccinates and N-acyl sarcosinates. The commonly-used anionic surfactants are sodium and ammonium lauryl sulfates, sodium and ammonium laureth sulfate and alpha olefin sulfonates. Anionic surfactants are generally present in the compositions of the present invention at about 0.1% to about 15%, preferably, about 0.5% to about 10%.

The nonionic surfactants that can be used in the present invention include the wide variety of ethoxylated alcohols, nonoxynols, alkanolamides, alkyl stearates, alkyl palmitates and alkylpolyglucosides. Examples of the commonly-used nonionic surfactants are cetyl alcohol, stearyl alcohol, oleyl alcohol; the various types of ethoxylated alkylphenols; lauramide diethanolamide (DEA); lauramide monoethanolamide (MEA); isopropyl palmitate, isopropyl stearate and decylpolyglucoside. Nonionic surfactants are generally present in the compositions of the present invention at about 0.1 % to about 15%, preferably, about 0.5% to about 10%.

The compositions in accordance with the present invention may also contain one or more quaternary ammonium compounds that provide hair conditioning effects. The quaternary ammonium compounds can be monomeric or polymeric quaternary ammonium compounds. Nonlimiting examples of such compounds include cetyltrimonium chloride, stearyl trimonium chloride, benzalkonium chloride, behentrimonium chloride and a variety of polyquaterniums. The quaternary ammonium compounds are generally present in the compositions of the present invention at about 0.1% to about 10%, preferably, about 0.5% to about 5%.

Amphoteric surfactants that can be incorporated in the compositions of the present invention belong to the class of surface active chemicals that possess a positive and a negative charge in the same molecule and behave as a cation, an anion, or both, depending upon the pH of the medium and the nature of the amphoteric molecule. In general, the positive charge is located on a nitrogen, while the negative charge is carried by a carboxyl or sulfonate group. There are a large number of amphoteric surfactants that are suitable for use in the present invention, including, for example, the well-known betaines, sultaines, glycinates and propionates that may generally be represented by the following structural formulae shown below:

1. Betaines:

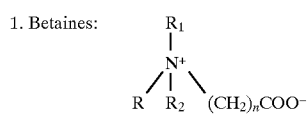

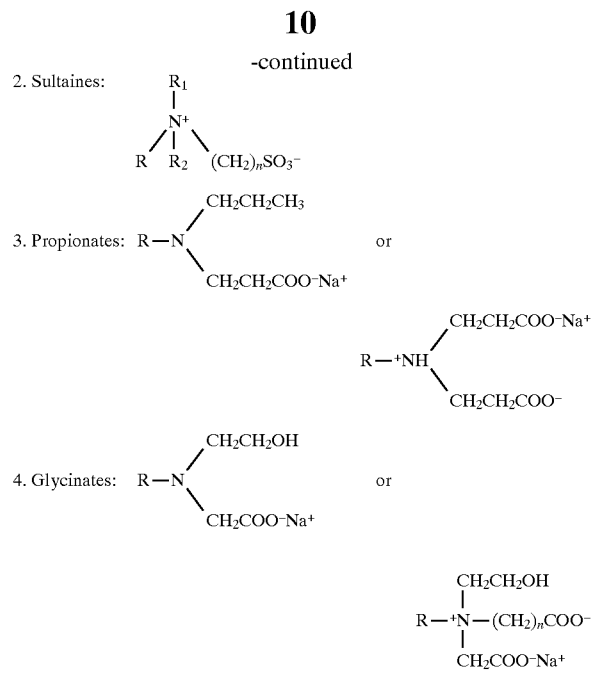

In these formulae, R is an alkyl or alkylamide group containing from about 10 to about 20 carbon atoms. $R_1$ and $R_2$ are alkyl or hydroxyalkyl groups, which may be the same or different, and contain up to about five carbon atoms; n is a positive integer from one to about five.

The selection of the amphoteric surfactant or mixture of surfactants for use in the present compositions and methods is not critical. The surfactant may be selected from among those suggested above, or from any of a number of other known amphoteric surfactants. The amount of amphoteric surfactant in the compositions of the present invention is normally from about 0.5% to about 15%, preferably, about 2% to about 10%.

Depending on the final formulated preparation, the compositions in accordance with invention may be weakly acidic, neutral or alkaline. In particular, the pH of the prepared compositions can range from about 5 to about 11. Preferred is a pH range of about 8 to 10. Any of a wide variety of alkaline reagents can be used to adjust the pH of the hair coloring compositions. Such alkaline reagents include ammonium hydroxide, potassium or calcium hydroxide, sodium or potassium carbonate, sodium phosphate, sodium silicate, guanidine hydroxide, or any one of the alkylamines or alkanolamines, for example, ethylamine, triethylamine, trihydroxymethylamino amine, ethanolamine, diethanolamine, aminomethyl propanol, aminomethyl propanediol and the like. The preferred alkaline reagents are ammonium hydroxide, sodium carbonate and ethanolamine. With the reagents listed above, the selected pH will generally be achieved if the composition contains an alkaline agent in an amount from about 0.1% to about 15%, preferably, about 0.5% to about 5%.

The application of the dyeing components is carried out by methods familiar to those in the art, for example, by mixing the hair dyeing preparation with an oxidant shortly before use, or at the time of applying the mixture onto the hair. On the hair, the compositions form a stable formulation with enough consistency and body to remain on the hair without dripping or running during the complete coloring period. The primary intermediate and coupler, i.e. the dye precursors, diffuse rapidly into the hair together with the oxidizing agent, or developer. The dyes form within the hair fiber, and since they are large molecules, remain in the hair so that the color change is permanent. The term "permanent" means the dye does not readily wash out of the hair with ordinary shampoos. At the end of coloring application (e.g., approximately 5 to 45 minutes, preferably, approximately 10 to 30 minutes), the composition is washed from the hair with an ordinary water rinse followed by a shampoo. The application temperature is in the range of about 15° C. to 50° C.

The 1-(4-aminophenyl) pyrrolidines, and cosmetically-acceptable derivatives and salts thereof, are soluble in water and have a long shelf life, particularly as constituents of the hair dyeing preparations in accordance with the invention. These primary intermediates, of which 1-(4-aminophenyl) pyrrolidine and 1-(4-amino-3-methylphenyl) pyrrolidine are preferred, should be present in the hair dyeing preparations in an amount of approximately 0.1% to approximately 10%, preferably, approximately 0.1% to approximately 5%. The total quantity of oxidative colorant, consisting of dye component(s) and coupling component(s) will suitably amount to approximately 0.1% to approximately 20%, and preferably, approximately 0.5% to approximately 15% of the composition.

The hair dyeing compounds in accordance with the invention will offer a wide range of varying color tints depending upon the type and composition of the colorant constituents. The color tints are distinguished herein by their particular intense and lasting color. The superior coloring properties of the hair dyeing compositions of the present invention are further evidenced by allowing grayed hair that has not been subjected to prior chemical damage to be covered without problems and with a depth and covering strength that, prior to the discovery of the primary intermediates of the present invention, had only been attained using the conventional PPD.

The compositions of this invention may be separately provided in a kit or packaged form ready for mixing by the user, either professional or consumer, to initiate the dyeing process. The kit provided in accordance with this invention comprises containers for housing the developer and the dye precursors. In the most convenient form, there will be two containers, one containing the primary dye intermediate and coupler, e.g., as a lotion; the other containing the oxidizing agent, also called the developer or developing agent.

The method of the invention comprises applying the mixture to the hair to be colored and allowing it to remain in contact with the hair until the desired hair color has been attained, after which time the composition is removed from the hair as described above.

EXAMPLES

The examples as set forth herein are meant to exemplify the various aspects of carrying out the invention and are not intended to limit the invention in any way.

EXAMPLE 1

1-(4-aminophenyl) pyrrolidine sulfate used in the oxidative hair dye compositions of the present invention was prepared in the following steps:

Step 1. Synthesis of 1-(4-nitrophenyl) pyrrolidine

Route 1: Synthesis from 4-fluoronitrobenzene:

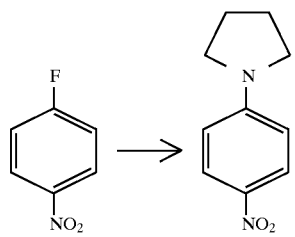

28.2 g (0.2 mole) 4-fluoronitrobenzene were combined with 21 ml (0.25 mole) pyrrolidine, 25.0 g $Na_2CO_3$, 200 ml $H_2O$, and the resultant mixture was refluxed with stirring. When TLC showed no evidence of starting material (ca. 3 hours), the mixture was cooled to ambient temperature and then placed in an ice-bath. The mixture was filtered, washed three times with cold $H_2O$ and dried in vacuo at 50° C. The final yield was 38.2 g (99%) of yellow solid.

Route 2: Synthesis from 4chloronitrobenzene:

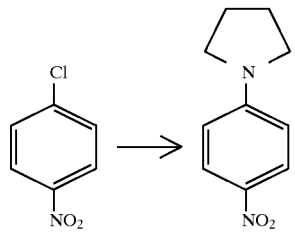

15.76 g (0.1 mole) 4-chloronitrobenzene were combined with 18.5 ml (0.22 mole) pyrrolidine, 11.0 g $Na_2CO_3$, 25 ml 2-propanol and 25 ml $H_2O$, and the resultant mixture was refluxed with stirring. When TLC showed no evidence of starting material (ca. 14 hours), 75 ml $H_2O$ were added, the mixture was refluxed for 1 hour, cooled to ambient temperature and placed in an ice-bath. The cold mixture was filtered, washed 5 times with cold $H_2O$ and dried in vacuo at 50° C. The final yield was 19.05 g (99%) of yellow solid.

Step 2. Synthesis of 1-(4-aminophenyl) pyrrolidine sulfate:

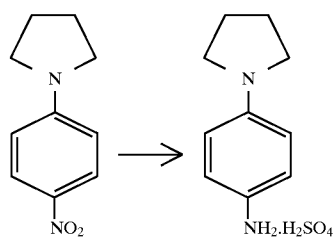

378.8 g (1.96 moles) 1-(4-nitrophenyl)pyrrolidine, 12.0 g Darco KB carbon, and 10% palladium on carbon (Pd/C) were suspended in 1300 ml ethanol and hydrogenated on a Parr apparatus at 60 psi. When $H_2$ uptake ceased and the reaction was complete, the mixture was filtered through filter aid and the resulting "cake" solid was washed 3 times with ethanol (50 ml/wash). The filtrate was stirred in an ice/acetone bath and a cold solution of concentrated $H_2SO_4$ (204 g (2 moles)) in 150 ml ethanol was added dropwise over 1 hour. The resultant precipitate was filtered, washed 4 times with ethanol (100 ml/wash) and dried in vacuo at 50° C. The final yield was 325 g (63%) of white solid. MS (solid probe): m/e 162 (free base).

As appreciated by those having skill in the art, additional synthetic routes, such as nitration or nitrosation of 1-phenylpyrrolidine or its analogs, followed by reduction, may also be used. In addition, other reduction techniques, such as Zn/HCl, may be used, as can other precious metal catalysts, such as Pt/C.

EXAMPLE 2

Substituted 1-(4-amino-2-methylphenyl) pyrrolidine sulfate, used in the oxidative hair dye compositions of the present invention, was prepared as follows:

Synthesis of 1-(4-amino-2-methylphenyl)pyrrolidine sulfate:

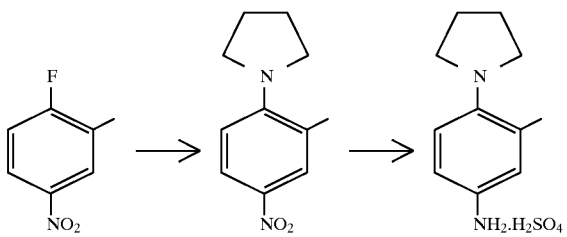

15.5g (0.1 mole) 2-fluoro-5-nitrotoluene, 25 ml (0.3 mole) pyrrolidine, 11.0 g $Na_2CO_3$ were combined with 50 ml 2-ethoxyethanol and refluxed with stirring. When the TLC showed no evidence of starting material (ca. 2 hours), the mixture was poured onto ice. The precipitate was filtered, washed 5 times with cold $H_2O$, and dried on filter paper for 2 hours. The resulting solid was mixed with 125 ml 2-propanol, 10% Pd/C, and hydrogenated at 60 psi on a Parr apparatus. The mixture was filtered through filter-aid and stirred with external cooling in an ice/acetone bath. A cold solution of 10.7 g (0.105 mole) concentrated $H_2SO_4$ in 15 ml 2-propanol was added dropwise over 15 minutes. The resultant precipitate was filtered, washed 2 times with 2-propanol and dried in vacuo at 50° C. The final yield was 24.45 g (89%) of a light grey solid. MS (solid probe): m/e 176 (free base).

As will be appreciated by those having skill in the art and as described above in Example 1, alternative synthesis procedures may be used. Examples include using 2-chloro-5-nitrotoluene as the starting material, and nitrating or nitrosating 1-(2-methylphenyl)pyrrolidine followed by reduction.

EXAMPLE 3

1-(4-amino-3-methylphenyl) pyrrolidine sulfate used in the oxidative hair dye compositions of the present invention was prepared as follows:

Synthesis of 1-(4-amino-3-methylphenyl)pyrrolidine sulfate:

Step 1. Synthesis of 1-(4nitro-3-methylphenyl)pyrrolidine

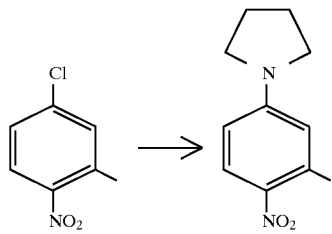

17.16 g (0.1 mole) 5-chloro-2-nitrotoluene were combined with 17 ml (0.2 mole) pyrrolidine, 11.0 g $Na_2CO_3$ and 60 ml 2-ethoxyethanol, and the resultant mixture was refluxed with stirring. When TLC showed no starting material (ca. 9 hours), the mixture was poured onto ice. The resultant precipitate was filtered, washed 5 times with cold $H_2O$ and dried in vacuo at 50° C. The final yield was 20.25 g (98%) of orange solid.

Step 2. Synthesis of 1-(4amino3-methylphenyl) pyrrolidine sulfate

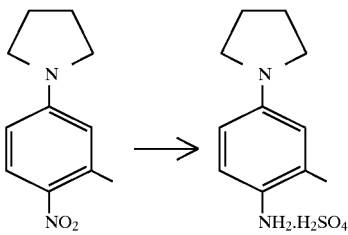

20.25 g (0.098 mole) 1-(4-nitro-3-methylphenyl) pyrrolidine were combined with 2 g Darco KB carbon, 200 ml 2-propanol and 5% Pd/C. The mixture was hydrogenated at 60 psi on a Parr apparatus. When reduction was complete, the mixture was filtered through filter aid and stirred with external cooling in an ice/acetone bath. A cold solution of 10.72 g (0.105 mole) concentrated $H_2SO_4$ in 20 ml 2-propanol was added dropwise and stirred for 1 hour. The mixture was filtered, washed 2 times with 2-propanol, and dried in vacuo at 50° C. The final yield was 22.3 g (83%) of off-white solid. MS (solid probe): m/e 176 (free base).

As mentioned hereinabove, alternative syntheses and reduction techniques may also be used. For example, 5-fluoro-2-nitrotoluene can be used as the starting material and 1-(3-methylphenyl)pyrrolidine can be nitrated or nitrosated and reduced.

EXAMPLES 4 TO 13

Hair dyeing compositions in accordance with the invention (Examples 4–13) were prepared as presented in Table 1. The compositions were in the form of lotions. Illustrative lotion compositions of this invention and the color results following the application of the compositions to gray hair are shown in Table 1.

TABLE 1

| Components | EXAMPLES: | | | | |
|---|---|---|---|---|---|
| | 4 | 5 | 6 | 7 | 8 |
| | Amounts of Components | | | | |
| | wt % | wt % | wt % | wt % | wt % |
| 1-(4-aminophenyl) pyrrolidine sulfate | 1.0 | 3.5 | 0.3 | 0.1 | 0.1 |
| p-phenylenediamine | — | — | — | — | 0.1 |
| N,N-bis(2-hydroxyethyl)-PPD sulfate | — | 0.5 | — | — | — |
| 4-aminophenol | — | — | 0.1 | — | 0.2 |
| 3-methyl-4-aminophenol | — | — | — | 0.2 | — |
| m-aminophenol | 0.5 | 1.5 | — | — | 0.1 |
| resorcinol | 0.5 | 1.5 | 0.4 | 0.2 | 0.5 |
| 1-naphthol | 0.1 | — | — | — | 0.1 |
| 2-methyl-1-naphthol | — | — | 0.1 | 0.1 | — |
| 4-amino-2-hydroxytoluene | — | — | — | 0.4 | 0.3 |
| m-phenylenediamine | — | 0.2 | — | — | — |
| isopropanol | 10 | 10 | 10 | 10 | 10 |
| propylene glycol | 15 | 15 | 15 | 15 | 15 |
| oleic acid | 14 | 14 | 14 | 14 | 14 |
| nonoxynol-2 | 9 | 9 | 9 | 9 | 9 |
| cocoamide DEA | 1 | 1 | 1 | 1 | 1 |
| ammonium hydroxide | 10 | 10 | 10 | 10 | 10 |
| sodium sulfite | 0.1 | 0.1 | 0.1 | 0.1 | 0.1 |

TABLE 1-continued

| | EXAMPLES: | | | | |
|---|---|---|---|---|---|
| | 4 | 5 | 6 | 7 | 8 |
| | Amounts of Components | | | | |
| Components | wt % | wt % | wt % | wt % | wt % |
| water | qs to 100 | qs to 100 | qs to 100 | qs to 100 | qs to 100 |
| Color Results on Gray Hair | Dark Brown | Blue Black | Light Brown | Auburn | Reddish Brown |

EXAMPLES 9 TO 13

Hair dyeing lotion compositions in accordance with the present invention (Examples 9 to 13) were prepared as presented in Table 2. Illustrative lotion compositions of this invention and the color results following the application of the composition to gray hair are presented in Table 2:

TABLE 2

| | EXAMPLES: | | | | |
|---|---|---|---|---|---|
| | 9 | 10 | 11 | 12 | 13 |
| | Amounts of Components | | | | |
| Components | wt % | wt % | wt % | wt % | wt % |
| 1-(4-aminophenyl) pyrrolidine sulfate | 1.0 | 3.5 | 0.3 | 0.1 | 0.1 |
| p-phenylenediamine | — | — | — | — | 0.1 |
| N,N-bis(2-hydroxyethyl)-PPD sulfate | — | 0.5 | — | — | — |
| 4-aminophenol | — | — | 0.1 | — | 0.2 |
| 3-methyl-4-aminophenol | — | — | — | 0.2 | — |
| m-aminophenol | 0.5 | 1.5 | — | — | 0.1 |
| resorcinol | 0.5 | 1.5 | 0.4 | 0.2 | 0.5 |
| 1-naphthol | 0.1 | — | — | — | 0.1 |
| 2-methyl-1-naphthol | — | — | 0.1 | 0.1 | — |
| 4-amino-2-hydroxytoluene | — | — | — | 0.4 | 0.3 |
| m-phenylenediamine | — | 0.2 | — | — | — |
| cocamidopropyl betaine | 10 | 10 | 10 | 10 | 10 |
| monoethanol amine | 2 | 2 | 2 | 2 | 2 |
| citric acid | 1 | 1 | 1 | 1 | 1 |
| ammonium hydroxide | 10 | 10 | 10 | 10 | 10 |
| sodium sulfite | 0.1 | 0.1 | 0.1 | 0.1 | 0.1 |
| water | qs to 100 | qs to 100 | qs to 100 | qs to 100 | qs to 100 |
| Color Results on Gray Hair | Dark Brown | Blue Black | Light Brown | Auburn | Reddish Brown |

EXAMPLES 14 TO 18

Hair dyeing gel compositions in accordance with the present invention (Examples 14 to 18) were prepared as presented in Table 3. Illustrative gel compositions of this invention and the color results following the application of the composition to gray hair are presented in Table 3:

TABLE 3

| | EXAMPLES: | | | | |
|---|---|---|---|---|---|
| | 14 | 15 | 16 | 17 | 18 |
| | Amounts of Components | | | | |
| Components | wt % | wt % | wt % | wt % | wt % |
| 1-(4-aminophenyl) pyrrolidine sulfate | 1.0 | 3.5 | 0.3 | 0.1 | 0.1 |
| p-phenylenediamine | — | — | — | — | 0.1 |
| N,N-bis(2-hydroxyethyl)-PPD sulfate | — | 0.5 | — | — | — |
| 4-aminophenol | — | — | 0.1 | — | 0.2 |
| 3-methyl-4-aminophenol | — | — | — | 0.2 | — |
| m-aminophenol | 0.5 | 1.5 | — | — | 0.1 |
| resorcinol | 0.5 | 1.5 | 0.4 | 0.2 | 0.5 |
| 1-naphthol | 0.1 | — | — | — | 0.1 |
| 2-methyl-1-naphthol | — | — | 0.1 | 0.1 | — |
| 4-amino-2-hydroxytoluene | — | — | — | 0.4 | 0.3 |
| m-phenylenediamine | — | 0.2 | — | — | — |
| cocamidopropyl betaine | 10 | 10 | 10 | 10 | 10 |
| monoethanol amine | 2 | 2 | 2 | 2 | 2 |
| oleic acid | 5 | 5 | 5 | 5 | 5 |
| decyl polyglucoside | 5 | 5 | 5 | 5 | 5 |
| ammonium hydroxide | 10 | 10 | 10 | 10 | 10 |
| sodium sulfite | 0.1 | 0.1 | 0.1 | 0.1 | 0.1 |
| water | qs to 100 | qs to 100 | qs to 100 | qs to 100 | qs to 100 |
| Color Results on Gray Hair | Dark Brown | Blue Black | Light Brown | Auburn | Reddish Brown |

EXAMPLE 19

Table 4 presents the results of the hair dyeing performance of the 1-(4-aminophenyl) pyrrolidine primary intermediate (Compound 6 in Table 4) in compositions of the invention compared with that of PPD (Compound 1 in Table 4) and various analogs of PPD, using 3-aminophenol as coupling agent (Table 4). For these evaluations, equimolar amounts of the primary dye intermediate (0.2M) and the coupling agent (0.2 M) were used (for examples, see Tables 1–3). The primary intermediate and coupling agent were mixed with 20 vol. hydrogen peroxide immediately before use, and the mixture was subsequently applied to blended gray hair swatches. The treatment period was for 30 minutes at room temperature; thereafter, the dyed hair was rinsed with water and dried.

In Table 4, "L", "a", and "b" represent the standard Hunter Tristimulus values which measure the depth and tonality of the color. In the Hunter method, the parameters a and b may be positive or negative and define the chromatic condition of the hair. Thus, the more positive the a value, the greater the redness of the hair, while negative a values indicate greenness. Similarly, positive b values indicate yellowness, while negative b values indicate blueness. The L parameter is a measure of color intensity and has a value of 0 for absolute black to 100 for absolute white.

TABLE 4

Hair Dyeing Performance of PPD Versus Various 1-(4-aminophenyl) pyrrolidine Compounds of the Present Invention (i.e., PPD Analogs) With 3-Aminophenol As Coupling Compound

| Dye Compound No. | Chemical Name of Dye Compound Used As Primary Intermediate | L | a | b | ΔH* | ΔE* |
|---|---|---|---|---|---|---|
| 1 | PPD | 21.0 | 0.4 | −0.5 | | |
| 2 | 2-methyl PPD | 22.0 | 1.0 | 0.1 | 0.85 | 1.31 |

TABLE 4-continued

Hair Dyeing Performance of PPD Versus Various 1-(4-aminophenyl) pyrrolidine Compounds of the Present Invention (i.e., PPD Analogs) With 3-Aminophenol As Coupling Compound

| Dye Compound No. | Chemical Name of Dye Compound Used As Primary Intermediate | L | a | b | ΔH* | ΔE* |
|---|---|---|---|---|---|---|
| 3 | 2-(2-hydroxyethyl) PPD | 26 | 1.6 | 3.0 | 3.7 | 6.22 |
| 4 | 2-chloro PPD | 25.5 | 2.9 | −1.0 | 2.55 | 5.17 |
| 5 | N,N-bis(2-hydroxyethyl) PPD | 23.5 | 0.4 | −3.8 | 3.3 | 3.09 |
| 6 | 1-(4-aminophenyl) pyrrolidine | 21.2 | 0.5 | −1.0 | 0.51 | 0.55 |
| 7 | 1-(4-aminophenyl) piperidine | 27.1 | 1.8 | 2.2 | 3.04 | 6.82 |
| 8 | 4-(4-aminophenyl) morpholine | 27.1 | 3.8 | 2.0 | 4.22 | 7.42 |
| 9 | N,N-dimethyl PPD | 25.9 | 0.1 | 1.6 | 2.12 | 5.34 |

*versus PPD

From the data presented in Table 4, it can be observed that compound 6 (1-(4-aminophenyl) pyrrolidine) of the present invention is the closest match to PPD (compound 1) in color tone and intensity when coupled with 3-aminophenol. The difference in color tone is measured by $\Delta H=[(\Delta a)^2+(\Delta b)^2]^{1/2}$ and total color difference, as determined by $\Delta E=[(\Delta a)^2+(\Delta b)^2+(\Delta L)^2]^{1/2}$. Both the ΔH and the ΔE values for any compound versus PPD are the smallest for compound 6 (i.e., 1-(4-aminophenyl) pyrrolidine) of the invention. Compound 2, (2-methyl PPD), the ring-substituted intermediate conventionally used in commercial hair dye products, is the next closest. None of the other compounds are as close to PPD in either intensity or tonality, including compound 3 (2-(2-hydroxyethyl) PPD). These results demonstrate that compound 6 of the present invention can be employed as a replacement, in whole or in part, for PPD with little or no difference in tone or intensity of color.

The formation of an intense neutral color from the 1-(4-aminophenyl) pyrrolidine compound combined with 3-aminophenol, as coupler, was completely unexpected prior to the present invention, since this color is far different from that formed by close chemical analogs of 1-(4-aminophenyl) pyrrolidine, i.e., compounds 5, 7, 8 and 9, with 3-aminophenol. Indeed, although the aforementioned compounds are N,N-disubstituted or N-cyclic compounds, similar to 1-(4-aminophenyl) pyrrolidine, only 1-(4-aminophenyl) pyrrolidine matches virtually identically with the N-unsubstituted PPD in color formation. These findings were evidenced both for the difference in color tone (i.e., ΔH versus PPD) and for the variation in total color (ΔE versus PPD).

EXAMPLE 20

In this example, the hair dyeing performance of unsubstituted 1-(4-aminophenyl) pyrrolidine (compound 6), 1-(4-amino-2-methylphenyl) pyrrolidine (compound 10) and 1-(4-amino-3-methylphenyl) pyrrolidine (compound 11), as primary intermediates in the compositions of the invention, was evaluated in combination with the different coupling agents presented in Table 5.

For these analyses, blended and bleached hair swatches were dyed for 30 minutes with compositions comprising 0.2M primary intermediate and 0.2M coupler in a cosmetically acceptable hair dye base (for examples, see Tables 1–3) plus 20 vol. $H_2O_2$, followed by a water rinse and air drying.

TABLE 5

Hair Color Products Obtained From 1-(4-Aminophenyl) Pyrrolidines of the Present Invention Reacted With Various Couplers

| | | Color | |
|---|---|---|---|
| Compound | Coupler | Blended Grey | Bleached |
| 6 | 3-aminophenol | Bluish black | Neutral black |
| 6 | resorcinol | Dark brown | Neutral black |
| 6 | 2-methylresorcinol | Dark reddish | Neutral black |
| 6 | 2-hydroxy-4-amino-toluene | Violet black | Neutral black |
| 6 | 1-naphthol | Blue | Purplish black |
| 6 | 2-methyl-1-naphthol | Violet blue | Dark violet blue |
| 10 | 3-aminophenol | Medium brown | Dark brown |
| 10 | 2-hydroxy-4-amino-toluene | Violet | Dark violet |
| 10 | 1-naphthol | Violet blue | Deep blue |
| 11 | 3-aminophenol | Bluish black | Neutral black |
| 11 | 2-hydroxy-4-amino-toluene | Dark blue | Bluish black |
| 11 | 1-naphthol | Bright blue | Violet |
| 11 | resorcinol | Reddish brown | Dark brown |
| 11 | 2-methylresorcinol | Medium brown | Dark warm brown |
| 11 | 2-methyl-1-napthol | Navy blue | Violet blue |
| 6 | 2-(2,4-diaminophenoxy) ethanol | Dark blue | Neutral black |
| 11 | 2-(2,4-diaminophenoxy) ethanol | Blue | Bluish black |

In Table 5, compound 6 is unsubstituted 1-(4-aminophenyl) pyrrolidine, compound 10 is 1-(4-amino-2-methylphenyl) pyrrolidine and compound 11 is 1-(4-amino-3-methylphenyl) pyrrolidine. The structures of compounds 10 and 11 are shown as Formulae II and III, respectively, in the Detailed Description of the Invention hereinabove.

The results from these evaluations demonstrate that the color produced using the unsubstituted and substituted 1-(4-aminophenyl) pyrrolidine compounds of the invention, namely 1-(4-aminophenyl) pyrrolidine, 1-(4-amino-2-methylphenyl) pyrrolidine and 1-(4-amino-3-methylphenyl) pyrrolidine, as primary intermediates in hair dye compositions, was intense and vivid. In addition, different coloration and nuances could be achieved using the compounds of the invention as primary intermediates in combination with various conventionally-used couplers. The newly-discovered compound 11 afforded surprising performance in coloring both gray and bleached hair compared with the coloration produced by compound 10 using the same coupling agents. Further, the results presented in Table 5 exemplify novel hair colors which are the reaction products of compounds of the present invention, e.g., compounds 6, 10 and 11, with particularly suitable couplers.

The contents of all patents, patent applications, published articles, books, reference manuals and abstracts cited herein are hereby incorporated by reference in their entirety to more fully describe the state of the art to which the invention pertains.

As various changes can be made in the above-described subject matter without departing from the scope and spirit of the invention, it is intended that all subject matter contained in the above description, shown in the accompanying drawings, or defined in the appended claims be interpreted as descriptive and illustrative, and not in a limiting sense. Many modifications and variations of the present invention are possible in light of the above teachings. It is therefore to be understood that within the scope of the appended claims, the invention may be practiced otherwise than as specifically described.

What is claimed is:

1. In a composition for the oxidative coloring of hair, said composition containing a primary dye intermediate, a coupling compound, a cosmetically acceptable oxidizing agent selected from the group consisting of hydrogen peroxide, urea peroxide, melamine peroxide, perborates, and percarbonates, and a cosmetically acceptable vehicle, wherein said primary dye intermediate and said coupling compound form an oxidative hair dye in the presence of said cosmetically acceptable oxidizing agent, the improvement which comprises said primary dye intermediate is a 1-(4-aminophenyl) pyrrolidine, or a cosmetically acceptable salt thereof, having formula I:

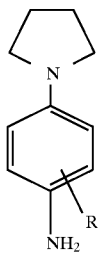

wherein R is selected from the group consisting of hydrogen, $C_1$–$C_6$ alkyl and $C_1$–$C_5$ mono or polyhydroxyalkyl.

2. The composition according to claim 1, wherein R is hydrogen or methyl.

3. The composition according to claim 2, wherein R is hydrogen.

4. The composition according to claim 2, wherein R is methyl.

5. The composition according to claim 4, wherein said methyl is at the 2-position of the phenyl ring of said 1-(4-aminophenyl) pyrrolidine or cosmetically acceptable salt thereof.

6. The composition according to claim 4, wherein said methyl is at the 3-position of the phenyl ring of said 1-(4-aminophenyl) pyrrolidine or cosmetically acceptable salt thereof.

7. The composition according to claim 1, wherein R is hydrogen, $C_1$–$C_2$ alkyl, or $C_1$–$C_3$ monohydroxyalkyl.

8. The composition according to claim 1, wherein said 1-(4-aminophenyl) pyrrolidine is present in an amount of about 0.01% to about 10%, by weight, based on the total weight of the composition.

9. The composition according to claim 1, wherein said coupling compound is present in an amount of about 0.1% to about 10%, by weight, based on the total weight of the composition.

10. The composition according to claim 8, wherein said 1-(4-aminophenyl) pyrrolidine primary intermediate is present at about 0.1% to about 5%, by weight, based on the total weight of the composition.

11. The composition according to claim 9, wherein the coupling compound is present in an amount of about 0.1% to about 5%, by weight, based on the total weight of the composition.

12. The composition according to claim 1, further including one or more additional dye components selected from the group consisting of p-phenylenediamine and cosmetically acceptable derivatives thereof; p-aminophenols and cosmetically acceptable derivatives thereof; ortho developers and cosmetically acceptable derivatives thereof; phenols and cosmetically acceptable derivatives thereof; resorcinols and cosmetically acceptable derivatives thereof; m-phenylenediamines and cosmetically acceptable derivatives thereof; m-aminophenols and cosmetically acceptable derivatives thereof; and heterocyclic derivatives.

13. The composition according to claim 1, wherein said coupling compound is selected from the group consisting of 3-aminophenol, resorcinol, 2-methylresorcinol, 2-hydroxy-4-aminotoluene, 1-naphthol, 2-methyl-1-naphthol and 2-(2, 4-diaminophenoxy)ethanol.

14. The composition according to claim 1, wherein said oxidizing agent is hydrogen peroxide.

15. An oxidative hair dye product produced by reacting, in a cosmetically acceptable vehicle and in the presence of a cosmetically acceptable oxidizing agent selected from the group consisting of hydrogen peroxide, urea peroxide, melamine peroxide, perborates, and percarbonates, a coupling compound and a 1-(4-aminophenyl) pyrrolidine, or a cosmetically acceptable salt thereof, having the formula I:

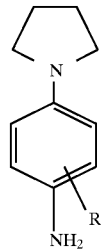

wherein R is selected from the group consisting of hydrogen, $C_1$–$C_6$ alkyl and $C_1$–$C_5$ mono or polyhydroxyalkyl.

16. The hair dye product according to claim 15, wherein R is hydrogen or methyl.

17. The hair dye product according to claim 16, wherein R is hydrogen.

18. The hair dye product according to claim 16, wherein R is methyl.

19. The hair dye product according to claim 18, wherein said methyl is at the 2-position of the phenyl ring of said 1-(4-aminophenyl) pyrrolidine or cosmetically acceptable salt thereof.

20. The hair dye product according to claim 18, wherein said methyl is at the 3-position of the phenyl ring of said 1-(4-aminophenyl) pyrrolidine or cosmetically acceptable salt thereof.

21. The hair dye product according to claim 15, wherein R is hydrogen, $C_1$–$C_2$ alkyl, or $C_1$–$C_3$ monohydroxyalkyl.

22. The hair dye product according to claim 15, wherein said coupling compound is selected from the group consisting of 3-aminophenol, 2-hydroxy-4-aminotoluene, resorcinol, 2-methylresorcinol, 1-naphthol, 2-methyl-1-napthol and 2-(2,4-diaminophenoxy) ethanol.

23. A hair dye product formed-by reacting equimolar amounts of (i) a 1-(4-aminophenyl) pyrrolidine, or a cosmetically acceptable salt thereof, having the formula I:

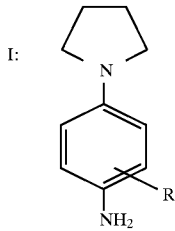

wherein R is selected from the group consisting of hydrogen, $C_1$–$C_6$ alkyl and $C_1$–$C_5$ mono or polyhydroxyalkyl, (ii) a coupling agent, and (iii) a cosmetically acceptable oxidizing agent selected from the group consisting of hydrogen peroxide, urea peroxide, melamine peroxide, perborates, and percarbonates, in a cosmetically acceptable vehicle.

24. The hair dye product according to claim 23, wherein R is hydrogen or methyl.

25. The hair dye product according to claim 24, wherein said methyl is at the 2-position of the phenyl ring of said 1-(4-aminophenyl) pyrrolidine or cosmetically acceptable salt thereof.

26. The hair dye product according to claim 24, wherein said methyl is at the 3-position of the phenyl ring of said 1-(4-aminophenyl) pyrrolidine or cosmetically acceptable salt thereof.

27. The hair dye product according to claim 23, wherein R is hydrogen, $C_1$–$C_2$ alkyl, or $C_1$–$C_3$ monohydroxyalkl.

28. The hair dye product according to claim 23, wherein said coupling agent is selected from the group consisting of 3-aminophenol, 2-hydroxy-4-aminotoluene, resorcinol, 2-methylresorcinol, 1-naphthol, 2-methyl-1-napthol and 2-(2,4-diaminophenoxy) ethanol.

29. A method for the oxidative coloring of a keratin fiber comprising contacting the fiber with a fiber coloring effective amount of a composition containing a 1-(4-aminophenyl) pyrrolidine, or a cosmetically acceptable salt thereof, having Formula I:

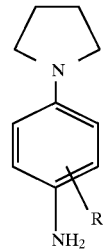

wherein R is selected from the group consisting of hydrogen, $C_1$–$C_6$ alkyl and $C_1$–$C_5$ mono or polyhydroxyalkyl, a coupling compound and a cosmetically acceptable oxidizing agent, in a cosmetically acceptable vehicle; and maintaining contact with the fiber until the fiber is colored.

30. The method according to claim 29 wherein the fiber is human hair.

* * * * *